(12) United States Patent
Juhn et al.

(10) Patent No.: US 11,602,308 B2
(45) Date of Patent: Mar. 14, 2023

(54) SYSTEM AND METHOD FOR INFORMING OF ATTACHMENT POSITIONS OF ECG ELECTRODES

(71) Applicant: Wellysis Corp., Seoul (KR)

(72) Inventors: Young Juhn, Seoul (KR); Byung Ki Moon, Seoul (KR); Jong Woo Kim, Seoul (KR); Rick Hongryul Kim, Seoul (KR); Jung Soo Kim, Seoul (KR); Jae Woo So, Seoul (KR)

(73) Assignee: WELLYSIS CORP., Seoul (KR)

( * ) Notice: Subject to any disclaimer, the term of this patent is extended or adjusted under 35 U.S.C. 154(b) by 245 days.

(21) Appl. No.: 17/193,723

(22) Filed: Mar. 5, 2021

(65) Prior Publication Data

US 2022/0133229 A1 May 5, 2022

(30) Foreign Application Priority Data

Oct. 29, 2020 (KR) .................. 10-2020-0141793

(51) Int. Cl.
| | | |
|---|---|---|
| A61B 5/339 | (2021.01) | |
| A61B 5/00 | (2006.01) | |
| A61B 5/28 | (2021.01) | |
| A61B 5/352 | (2021.01) | |
| A61B 5/36 | (2021.01) | |

(52) U.S. Cl.
CPC ............ *A61B 5/684* (2013.01); *A61B 5/0006* (2013.01); *A61B 5/28* (2021.01); *A61B 5/339* (2021.01); *A61B 5/352* (2021.01); *A61B 5/36* (2021.01); *A61B 5/741* (2013.01)

(58) Field of Classification Search
None
See application file for complete search history.

(56) References Cited

U.S. PATENT DOCUMENTS

| | | | | |
|---|---|---|---|---|
| 2009/0030307 A1* | 1/2009 | Govari | ................. | A61B 8/4254 600/424 |
| 2017/0105678 A1* | 4/2017 | Xue | ......................... | A61B 5/25 |

FOREIGN PATENT DOCUMENTS

| | | |
|---|---|---|
| KR | 10-2014-0050374 A | 4/2014 |
| KR | 10-2019-0128841 A | 11/2019 |
| KR | 10-2020-006813 A | 1/2020 |
| KR | 10-2134205 B | 7/2020 |

* cited by examiner

*Primary Examiner* — Kennedy Schaetzle
(74) *Attorney, Agent, or Firm* — Stein IP, LLC (57) ABSTRACT

Provided are a system and method for informing of attachment positions of electrocardiogram (ECG) electrodes to improve the quality of ECG data. The system includes a judgment indicator extractor configured to extract a plurality of judgment indicator values from ECG data obtained through ECG electrodes, a reference value setter configured to, in a user-specific reference value setting mode, collect the judgment indicator values for a plurality of pieces of ECG data extracted by the judgment indicator extractor and set user-specific reference values for each judgment indicator, a similarity determiner configured to, in an ECG measurement mode, determine similarity by comparing a plurality of judgment indicator values extracted by the judgment indicator extractor with the user-specific reference values, and an electrode attachment position guide configured to inform a user of attachment positions of the ECG electrodes according to a similarity determination result of each of the judgment indicator values.

16 Claims, 5 Drawing Sheets

SYSTEM AND METHOD FOR INFORMING OF ATTACHMENT POSITIONS OF ECG ELECTRODES

CROSS-REFERENCE TO RELATED APPLICATIONS

This application claims the benefit of Korean Application No. 10-2020-0141793, filed Oct. 29, 2020, in the Korean Intellectual Property Office. All disclosures of the document named above are incorporated herein by reference.

BACKGROUND

1. Technical Field

The present invention relates to an electrocardiogram (ECG) measurement system and more particularly, to a system and method for informing of the attachment positions of ECG electrodes required for improving the quality of ECG data.

2. Description of Related Art

Activity currents generated from cardiac muscle according to heartbeats may be guided to two appropriate points on the body surface and recorded by an ammeter, and a record of myocardial activity currents obtained in this way is referred to as an electrocardiogram (ECG).

An ECG check is performed on patients with symptoms, such as a chest pain or difficulty in breathing, and patients with a disease which affects the heart such as high blood pressure. An ECG check may be performed as a basic examination for checking cardiac functions of a preoperative patient before general anesthesia is administered.

ECG checks are generally performed with an ECG measurement device (or system). Such ECG measurement devices can be classified into various types of measurement devices according to places or purposes of use, and wearable patch-type ECG measurement devices are frequently used for everyday ECG monitoring.

Wearable patch-type ECG measurement devices are useful when a user (a diagnosis target) measures and transmits his or her own ECG to a hospital (or a doctor in charge) and the hospital receives and remotely checks the ECG.

In general, a user attaches ECG electrodes (or measurement electrodes) of a wearable patch-type ECG device to his or her body with the help of an expert at a hospital. Accordingly, when the measurement period is short, it is possible to collect accurate ECG data. However, when the measurement period is long, the user may detach the ECG electrodes from his or her body for a reason, such as showering, battery replacement, or the like, and then attach the ECG electrodes again. In this case, inaccurate ECG data is frequently collected.

According to the attachment positions of ECG electrodes, a disease to be diagnosed or predicted may vary. For this reason, the attachment positions of ECG electrodes should be accurate in order to increase accuracy in diagnosing a disease. Consequently, when a general user uses a patch-type ECG device without the help of an expert, a method of informing of the attachment positions of ECG electrodes is required for obtaining accurate ECG data.

PRIOR-ART DOCUMENTS

Patent Documents

Korean Patent Application Publication No. 10-2014-0050374 Korean Patent Application Publication No. 10-2020-0006813

SUMMARY

1. Technical Problem

A technical objective of the present invention is to provide a system and method for directly informing a user of the attachment positions of electrocardiogram (ECG) electrodes in order to obtain accurate ECG data.

Another technical objective of the present invention is to provide a system and method for directly informing a user of the attachment positions of ECG electrodes and only transmitting data required for disease diagnosis among pieces of ECG data obtained from the informed positions.

Still another technical objective of the present invention is to provide a system and method for generating reference signals, which are required for informing users of the attachment positions of electrodes, according to the users and allowing the reference signals to be used.

2. Solution to Problem

A system for informing of the attachment positions of electrocardiogram (ECG) electrodes according to the present invention includes: a judgement indicator extractor configured to extract a plurality of judgement indicator values from ECG data obtained through ECG electrodes, a reference value setter configured to, in a user-specific reference value setting mode, collect the judgement indicator values for a plurality of pieces of ECG data extracted by the judgement indicator extractor and set user-specific reference values for each judgement indicator, a similarity determiner configured to, in an ECG measurement mode, determine similarity by comparing a plurality of judgement indicator values extracted by the judgement indicator extractor with the user-specific reference values, and an electrode attachment position guide configured to inform a user of attachment positions of the ECG electrodes according to a similarity determination result of each of the judgement indicator values.

In the system including the above-described configuration, the reference value setter may set an average of each type of judgement indicator values as the user-specific reference value when an average variance of each type of judgement indicator values collected in the user-specific reference value setting mode is a reference value or less.

The reference value setter may enter the user-specific reference value setting mode which is activated according to a user command and activate the ECG measurement mode after setting of the user-specific reference values is completed.

Further, in the system including the above-described configuration, the similarity determiner, in the ECG measurement mode, may determine first similarity by comparing the values of the judgement indicators having potential values among the plurality of extracted judgement indicator values with the corresponding user-specific reference values.

In some cases, the similarity determiner may include an artificial intelligence model which determines, when it is determined that the judgement indicator values are not similar to the corresponding user-specific reference values as a first similarity determination result, similarity by determining whether all the plurality of extracted judgement indicators are present within a similarity range set through pre-learning, in the ECG measurement mode.

Meanwhile, the judgement indicator extractor, the reference value setter, the similarity determiner, and the electrode attachment position guide constituting the system may be a set of code data constituting an executable application which is installed on a user information terminal such as a smart watch or a smart phone with a communication function.

A method of informing of attachment positions of ECG electrodes according to the present invention, which is executable on an information terminal of a user who uses a wearable patch-type ECG measurement device, includes: a first operation of extracting a plurality of judgement indicator values from each of a plurality of pieces of ECG data transmitted from the wearable patch-type ECG measurement device for a certain time; a second operation of collecting the extracted judgement indicator values and setting a user-specific reference value for each judgement indicator; a third operation of determining similarity by comparing a plurality of judgement indicator values, which are extracted from ECG data transmitted from the wearable patch-type ECG measurement device, with the user-specific reference values after the user-specific reference values are set; and a fourth operation of informing a user of attachment positions of ECG electrodes according to a similarity determination result of each of the judgement indicator values.

In the method, when an average variance of each type of the collected judgement indicator values is a reference value or less, an average of each type of the judgement indicator values may be set as the user-specific reference value.

The first and second operations may be performed in a user-specific reference value setting mode which is activated according to a user command, and the third and fourth operations may be repeatedly performed as an ECG measurement mode after the user-specific reference values are set.

3. Advantageous Effects

According to the above-described solution, a system for informing of the attachment positions of electrocardiogram (ECG) electrodes according to an embodiment of the present invention recommends a change or adjustment of the attachment position of an ECG electrode even when the position at which the ECG electrode is attached by a healthcare worker is changed by a user. Accordingly, it is possible to obtain an ECG waveform at an accurate position.

In addition, the present invention only stores and transmits ECG data obtained at positions where ECG electrodes are initially attached by a healthcare worker and thus can solve problems which may be caused by transmitting inaccurate ECG data, for example, misdiagnosis, overload of transmission data, and running efficiency degradation of a memory for storing and managing ECG data.

DETAILED DESCRIPTION OF EMBODIMENTS

To clarify objectives, technical solutions, and advantages of the present invention, specific embodiments for implementing the present invention are described in detail below with reference to the accompanying drawings. These embodiments are described in sufficient detail to enable those of ordinary skill in the art to implement the present invention.

In the detailed description and claims of the present invention, the term "include" and its variants are not intended to exclude other technical features, additions, elements, or operations. Other objectives, advantages, and features of the present invention may be revealed partially from the specification and partially from the implementation of the present invention. The following examples and drawings may be provided as practical examples but are not intended to limit the present invention. Further, the present invention encompasses all possible combinations of the embodiments described herein. It is to be understood that the various embodiments of the present invention are different but are not necessarily mutually exclusive. In addition, it is to be understood that the position or arrangement of individual elements within each disclosed embodiment may be modified without departing from the spirit and scope of the present invention. Accordingly, the following detailed description is not to be taken in a limiting sense, and the scope of the present invention is defined only by the appended claims, appropriately interpreted, along with the full range of equivalents asserted by the claims.

Unless otherwise indicated in the specification or clearly contradicted in the context, an item indicated in the singular includes those in the plural unless otherwise required in the context. Also, in the following description of the present invention, when a detailed description of related known configurations or functions is determined to obscure the gist of the present invention, the detailed description will be omitted.

Among terms used below, a "user-specific reference value setting mode" is defined as a mode for setting, when electrocardiogram (ECG) electrodes of a wearable patch-type ECG device are attached to a body normally by a healthcare worker, judgement indicators extracted from an ECG waveform acquired at the attachment positions of the ECG electrodes as user-specific reference values. The user-specific reference value setting mode, which is one of operation modes, may be set according to a command of a user (healthcare worker).

Meanwhile, an "ECG measurement mode," which is another operation mode, is used after user-specific reference values are set. The ECG measurement mode is defined as a mode of comparing a plurality of judgement indicator values extracted from an ECG waveform with user-specific reference values and informing of the attachment positions of ECG electrodes. In such an ECG measurement mode, ECG data obtained from ECG electrodes may be transmitted to an ECG analysis device 300 according to predefined rules.

Figure 1:
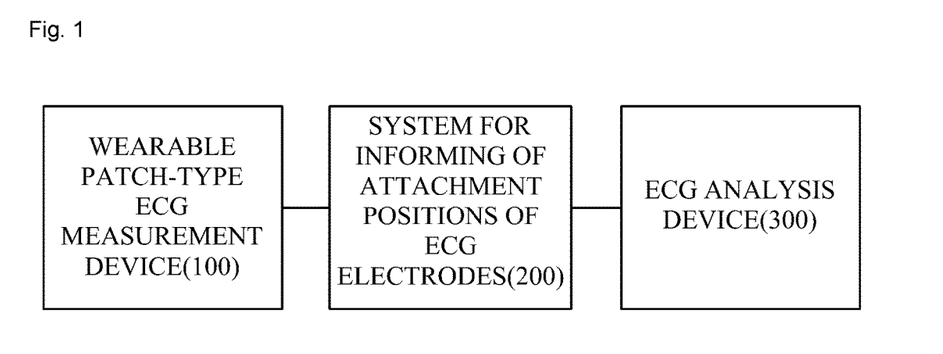
FIG. 1 shows surrounding configurations of a system for informing of the attachment positions of electrocardiogram (ECG) electrodes according to an exemplary embodiment of the present invention.
Figure 2:
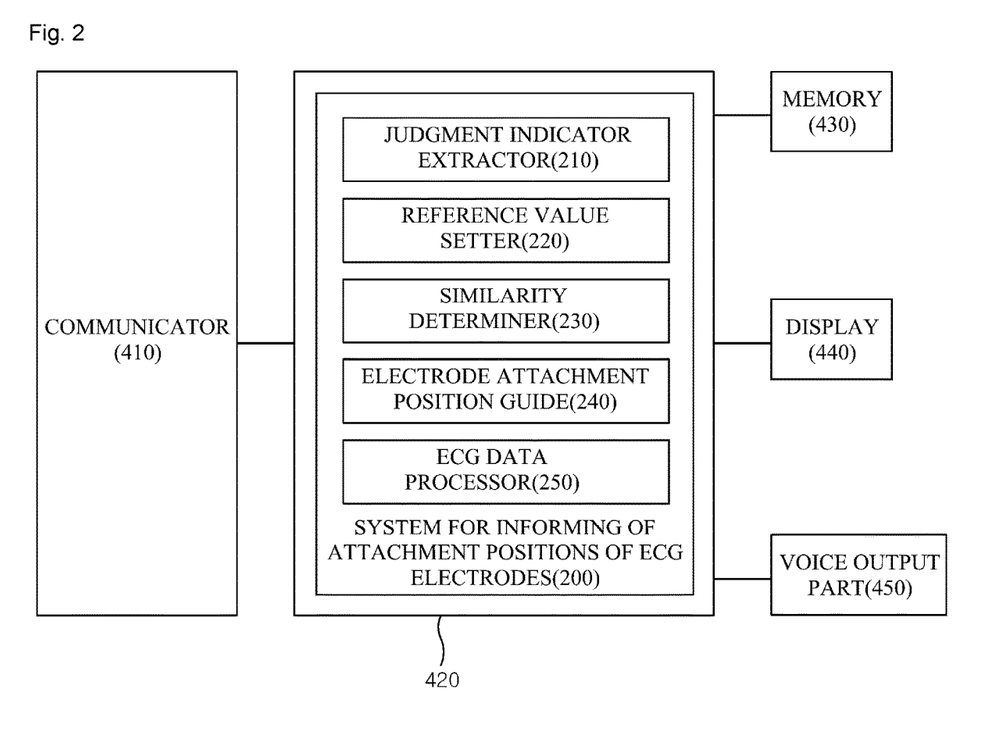
FIG. 2 is a block diagram of the system for informing of the attachment positions of ECG electrodes according to the exemplary embodiment of the present invention.

FIG. 1 shows surrounding configurations of a system 200 for informing of the attachment positions of ECG electrodes according to an exemplary embodiment of the present invention, and FIG. 2 is a block diagram of the system 200 for informing of the attachment positions of ECG electrodes according to the exemplary embodiment of the present invention.

The system 200 for informing of the attachment positions of ECG electrodes according to the exemplary embodiment of the present invention may be implemented as a set of code data constituting an executable application program which may be installed on a memory of a portable information terminal of a user who uses a wearable patch-type ECG measurement device 100, for example, a smart watch or a smart phone. The system 200 may also be implemented as a separate portable device with a communication function.

As shown in FIG. 1, the system 200 for informing of the attachment positions of ECG electrodes may inform a user of the attachment positions of ECG electrodes by receiving ECG data from the wearable patch-type ECG measurement device 100 capable of establishing a communication connection and processing the ECG data and may transmit the ECG data obtained from the wearable patch-type ECG measurement device 100 to the ECG analysis device 300 through another communication connection.

The wearable patch-type ECG measurement device 100 includes a plurality of ECG electrodes which are attached to a human body as patches and sense an ECG waveform, a signal preprocessor which removes noise from the ECG waveform obtained from the ECG electrodes, amplifies the signal, and converts the signal into digital ECG data, and a communicator which transmits the digital ECG data to the system 200 for informing of the attachment positions of ECG electrodes through wireless communication. The communicator may be a Bluetooth module employing Bluetooth low energy (BLE) communication.

The ECG analysis device 300 interprets the ECG data received through the system 200 for informing of the attachment positions of ECG electrodes on the basis of an automatic determination algorithm. This is only an example, and the ECG analysis device 300 may be equipment which simply displays received ECG data as an ECG waveform.

A configuration of the system 200 for informing of the attachment positions of ECG electrodes shown in FIG. 1 will be described in detail below with reference to FIG. 2.

For reference, among terms used below, the term "plurality of judgement indicators" is construed as indicators for determining whether an ECG waveform similar to that obtained at positions where ECG electrodes are initially attached by a healthcare worker is obtained.

In general, an ECG waveform includes P peaks based on atrial activity and QRST peaks based on ventricular activity. According to exemplary embodiments of the present invention, a plurality of judgement indicators include P peaks, R peaks, T peaks, RR intervals, QT intervals, QTc intervals, PR intervals, RT intervals, and QRS intervals of an ECG waveform. In addition to the three types of peaks, Q and S peaks may be further used.

Referring to FIG. 2, the system 200 for informing of the attachment positions of ECG electrodes includes:

a judgement indicator extractor 210 which extracts a plurality of judgement indicator values from ECG data obtained through ECG electrodes and transmitted by the wearable patch-type ECG measurement device 100;

a reference value setter 220 which collects judgement indicator values for a plurality of pieces of ECG data (the same meaning as ECG data of several periods) extracted by the judgement indicator extractor 210 and sets user-specific reference values for each judgement indicator in the user-specific reference value setting mode;

a similarity determiner 230 which determines similarity by comparing a plurality of judgement indicator values extracted by the judgement indicator extractor 210 with the user-specific reference values in the ECG measurement mode; and an electrode attachment position guide 240 which informs the user of the attachment positions of the ECG electrodes according to a similarity determination result of each of the judgement indicator values.

In the above-described configuration, the reference value setter 220 enters the user-specific reference value setting mode which is activated according to a user command and activates the ECG measurement mode after setting of user-specific reference values is completed. In other words, when attaching ECG electrodes of the wearable patch-type ECG measurement device 100 to a subject to be measured, a healthcare worker and the like sets an operation mode of the system 200 for informing of the attachment positions of ECG electrodes to the user-specific reference value setting mode by inputting the user command for newly setting user-specific reference values such that user-specific reference values may be set.

Also, the reference value setter 220 sets an average value of each judgement indicator as a user-specific reference value when an average variance of values of each judgement indicator collected in the user-specific reference value setting mode is a preset reference value or less.

For reference, it is assumed that when the user command is input, previously set user-specific reference values are automatically removed.

Meanwhile, the similarity determiner 230 may determine first similarity by comparing the values of judgement indicators having potential values (a P peak, an R peak, and a T peak) among a plurality of extracted judgement indicator values with corresponding user-specific reference values in the ECG measurement mode.

As a modified embodiment, the similarity determiner 230 may include an artificial intelligence learning model which determines, when it is determined that the judgement indicator values are not similar to the corresponding user-specific reference values as a result of the first similarity determination, similarity by determining whether all the plurality of extracted judgement indicators are present within a similarity range (95% or more) set through pre-learning in the ECG measurement mode.

The electrode attachment position guide 240 may inform of the attachment positions of ECG electrodes by displaying a body image, on which the attachment positions of ECG electrodes are marked, on an information terminal display 440 of the user of the ECG measurement device 100.

In some cases, the electrode attachment position guide 240 may inform of moved attachment positions of the ECG electrodes by a voice through an information terminal voice output part 450 of the user of the ECG measurement device 100.

The above-described judgement indicator extractor 210, reference value setter 220, similarity determiner 230, and electrode attachment position guide 240 may be a set of code data constituting an application program which is installed on the information terminal of the user who uses the ECG measurement device 100 and executed by a processor 420.

In addition, the system 200 for informing of the attachment positions of ECG electrodes may include an ECG data processor 250. For example, when an ECG waveform (construed to be the same as ECG data) measured in the ECG measurement mode before similarity determination has a phase inverted upside down, the ECG data processor 250 may invert the phase by multiplying the entire signal by −1. When noise occurs due to the user's movement or the like, the noise may be removed. However, such a noise removal process may be pre-processed by the wearable patch-type ECG measurement device 100.

A communicator 410 which has not been described in FIG. 2 is a communication module provided in the information terminal of the user and includes a Bluetooth module for transmitting and receiving data to and from the wearable patch-type ECG measurement device 100 and a mobile communication module for transmitting and receiving data to and from the ECG analysis device 300.

A memory 430, the display 440, and the voice output part 450 are elements provided in the information terminal of the user and used to store data and user-specific reference values required for a device control operation, display a body image on which the attachment positions of ECG electrodes are marked, or inform of moved attachment positions of the ECG electrodes by a voice.

Operation of the system 200 for informing of the attachment positions of ECG electrodes including the above-described elements will be described in detail below with reference to FIGS. 3 to 8.

Figure 3:
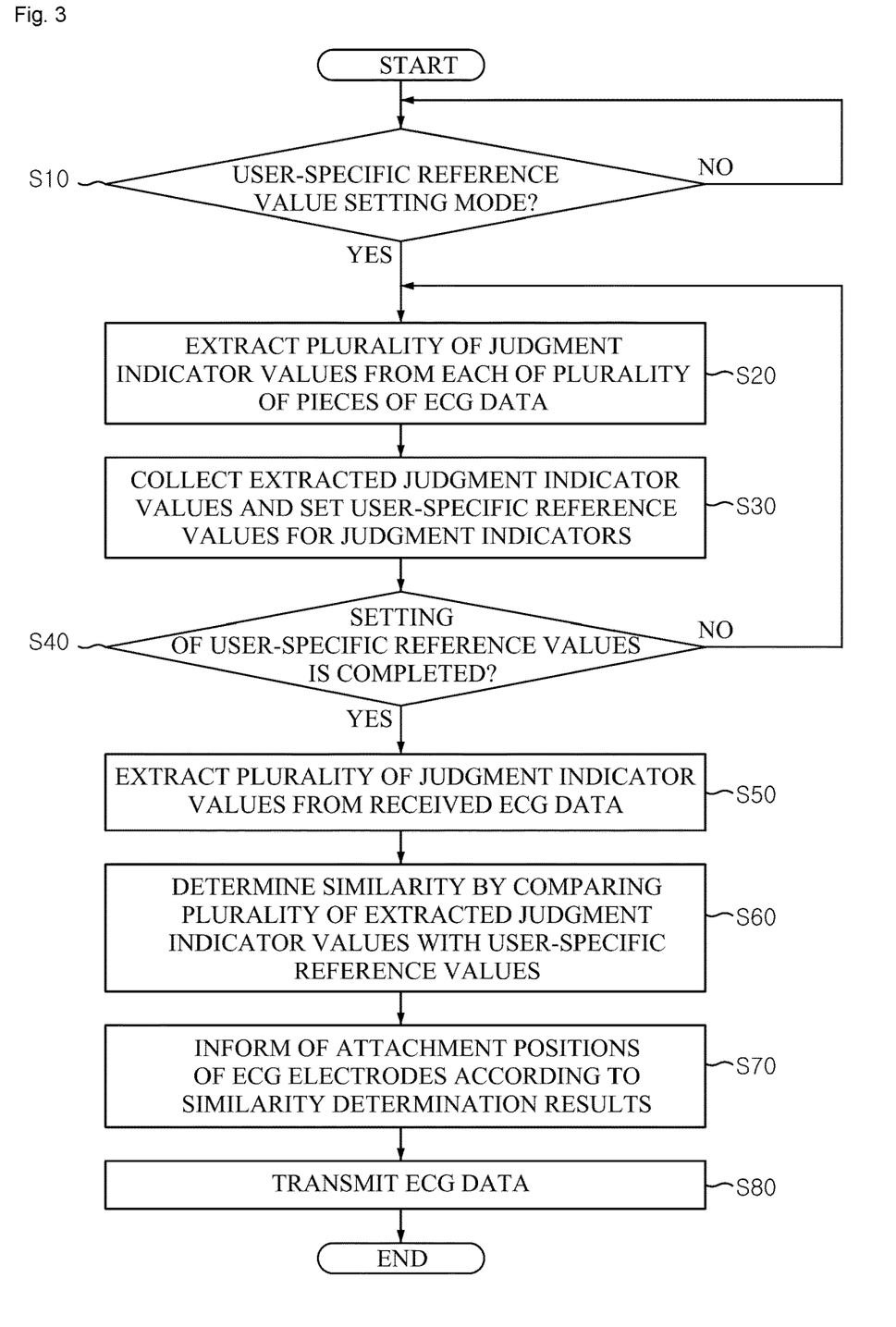
FIG. 3 is an operational flowchart for describing the operation of the system for informing of the attachment positions of ECG electrodes according to the exemplary embodiment of the present invention.
Figure 4:
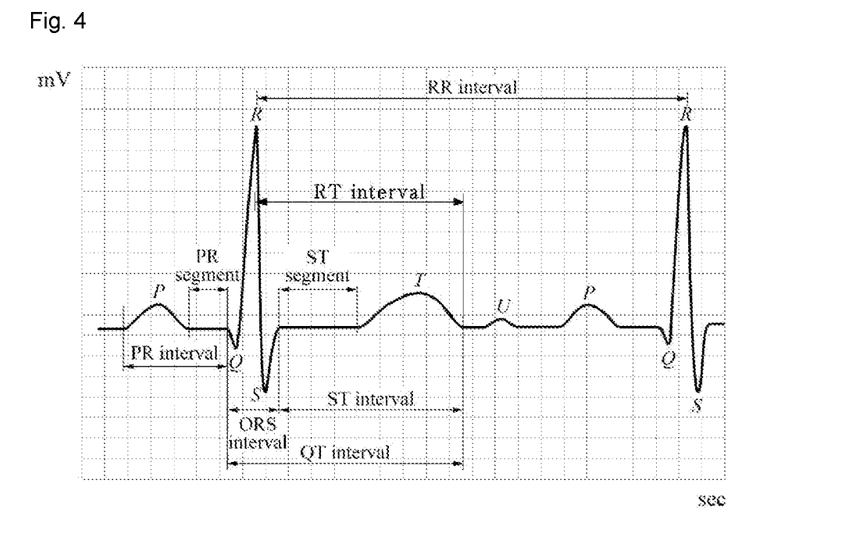
FIG. 4 is an ECG waveform diagram according to an exemplary embodiment of the present invention.
Figure 5:
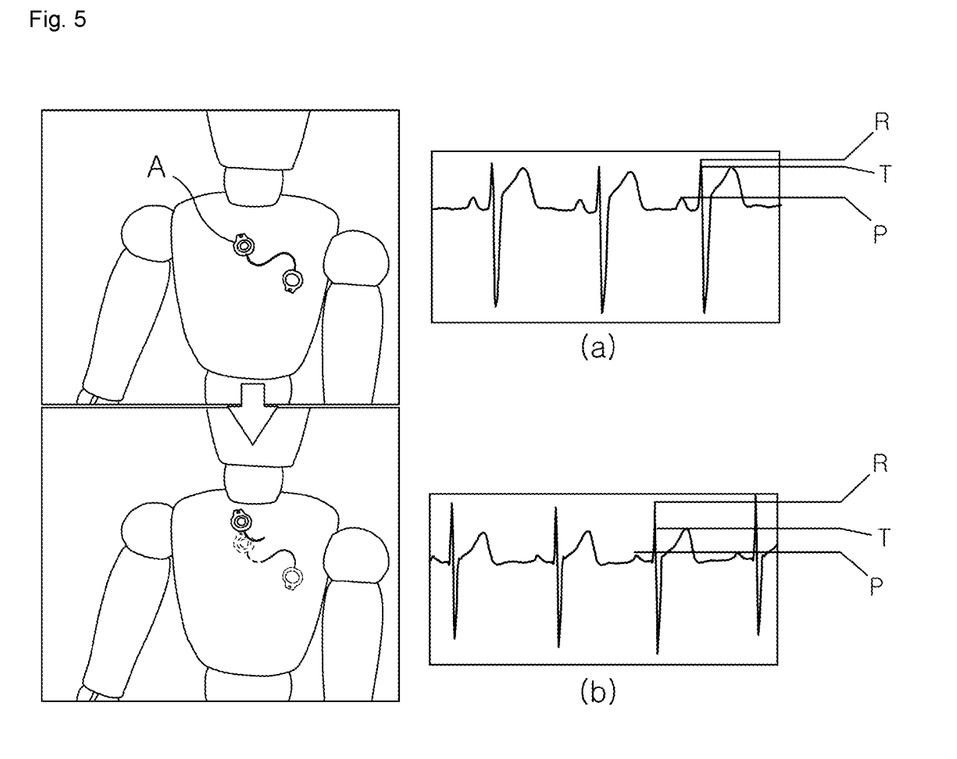
FIGS. 5 to 7 are diagrams for informing of the attachment positions of ECG electrodes according to an exemplary embodiment of the present invention.
Figure 6:
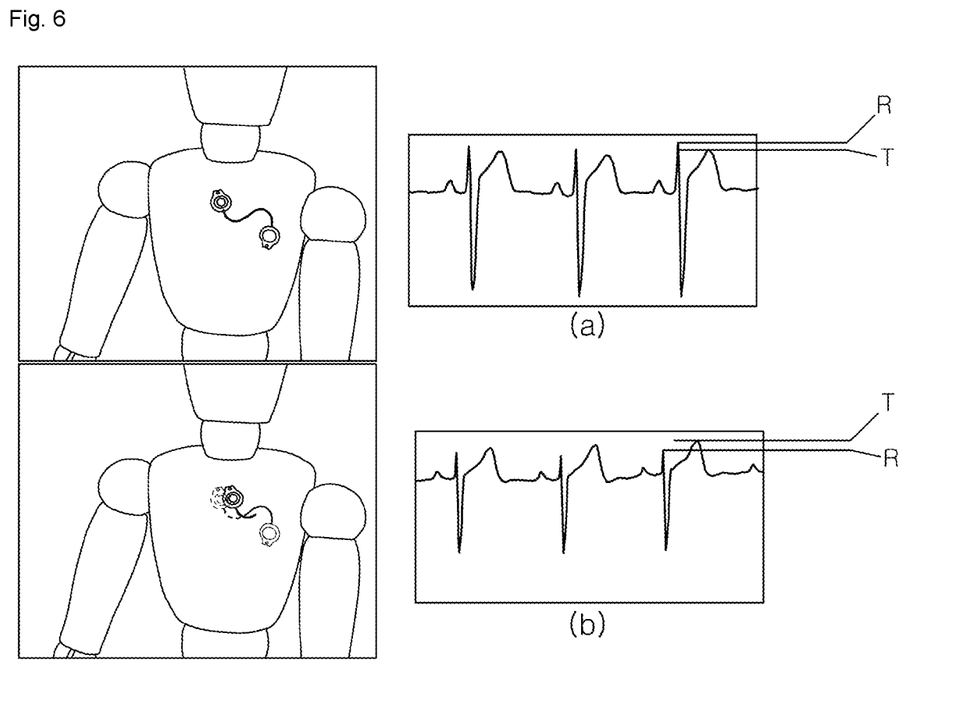
Figure 7:
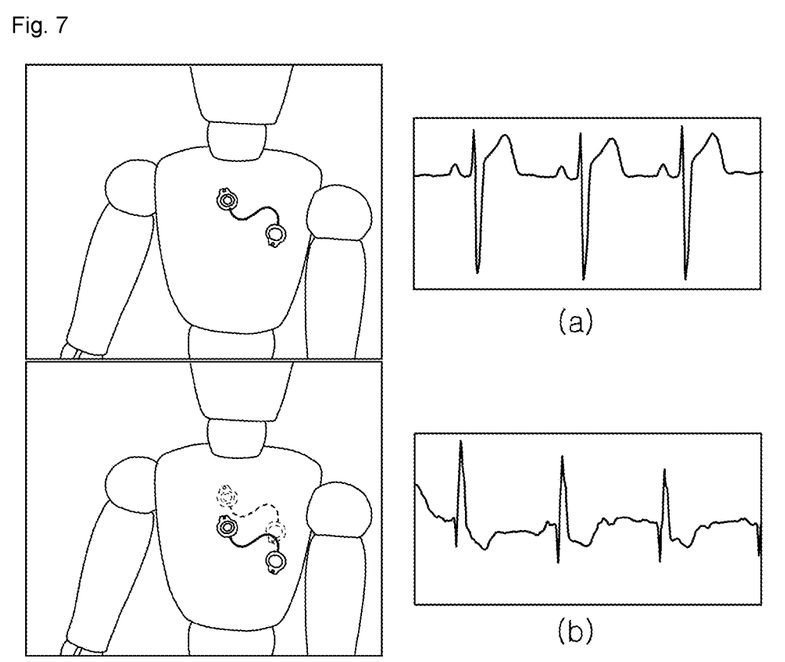
Figure 8:
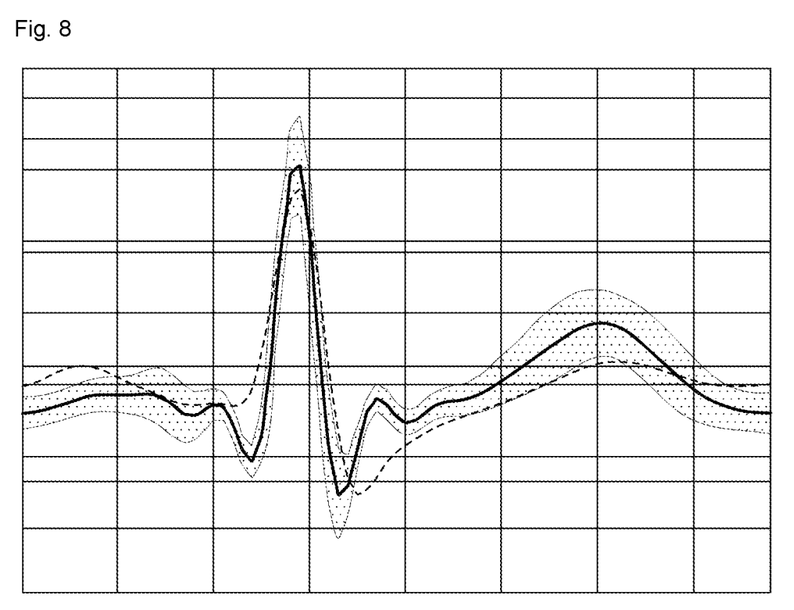
FIG. 8 is another ECG waveform diagram according to an exemplary embodiment of the present invention.

FIG. 3 is an operational flowchart illustrating operation of the system 200 for informing of the attachment positions of ECG electrodes according to the exemplary embodiment of the present invention, FIG. 4 is an ECG waveform diagram according to an exemplary embodiment of the present invention, FIGS. 5 to 7 are diagrams for informing of the attachment positions of ECG electrodes according to an exemplary embodiment of the present invention, and FIG. 8 is another ECG waveform diagram according to an exemplary embodiment of the present invention.

Referring to FIG. 3, first, a healthcare worker attaches ECG electrodes of the wearable patch-type ECG measurement device 100 to appropriate positions on the body of a subject to be measured and operates the ECG measurement device 100 to correctly diagnose a disease. To set positions at which the ECG electrodes are attached, the healthcare worker or a user executes the system 200 for informing of the attachment positions of ECG electrodes which is in the form of an application program installed on the user information terminal and inputs a user-specific reference setting command in a provided menu.

When there is a user-specific reference value setting command (operation S10), the reference value setter 220 sets the system operation mode to the user-specific reference value setting mode, and then the process proceeds to an operation S20. In the user-specific reference value setting mode, the judgement indicator extractor 210 extracts a plurality of judgement indicator values from ECG data transmitted from the wearable patch-type ECG measurement device 100 (operation S20). Assuming that the user-specific reference value setting mode lasts for a certain time (e.g., 30 minutes), the judgement indicator extractor 210 may extract a plurality of judgement indicator values from each of a plurality of pieces of ECG data for the certain time.

In the user-specific reference value setting mode, the reference value setter 220 collects judgement indicator values extracted by the judgement indicator extractor 210 at regular time intervals (e.g., every 10 minutes) and sets user-specific reference values for each of the judgement indicators (operation S30), and the set user-specific reference values may be stored in the memory 430 and managed.

According to a method of setting user-specific reference values, when an average variance of each type of collected judgement indicator values, for example, P peaks, R peaks, and T peaks which have potential values in the ECG waveform shown in FIG. 4 and RR intervals, QT intervals, QTc intervals, PR intervals, RT intervals, and QRS intervals which have time values in the ECG waveform, is a preset similarity setting reference value or less, an average value of each judgement indicator is set as a user-specific reference value. When an average variance of each type of collected judgement indicator values exceeds the preset similarity setting reference value, judgement indicator values are collected again for the regular time interval, and an average variance of the judgement indicator values is compared with the similarity setting reference value to set user-specific reference values. When a user-specific reference value is not set during a determined certain time (30 minutes), an instruction to reattach the ECG electrodes may be issued.

When setting of user-specific reference values is completed normally (operation S40), the reference value setter 220 shifts the system operation mode to the ECG measurement mode.

In the ECG measurement mode, the judgement indicator extractor 210 extracts, in real time, a plurality of judgement indicator values from ECG data transmitted from the wearable patch-type ECG measurement device 100 (operation S50). Then, the similarity determiner 230 determines first similarity by comparing the plurality of judgment indicator values extracted from the ECG data with the user-specific reference values (operation S60).

According to a first similarity determination method, values of judgment indicators having potential values (e.g., a P peak, an R peak, and a T peak) among a plurality of judgment indicator values extracted in real time are compared with corresponding user-specific reference values, and when the judgment indicator values have certain variances (the set reference values) or less, the judgment indicator values are determined to be similar to the corresponding user-specific reference values.

When the attachment positions of the ECG electrodes are changed from the initial attachment positions, P, R, and T peak values having potential values are changed by set reference values or more. Accordingly, the user may be informed of the attachment positions of the ECG electrodes through the changed values.

As an example, FIG. 5A may be assumed to be an ECG waveform obtained in the user-specific reference value setting mode, and FIG. 5B may be assumed to be an ECG waveform obtained through a positional change of an ECG electrode A. When an R peak is detected to be high and P and T peaks are detected to be low due to a positional change of the ECG electrode A as shown in FIG. 5B, an instruction to move the upper ECG electrode A (the upper node) in an upper direction by one knuckle may be issued.

As another example, in comparison with the ECG waveform shown in FIG. 6A, heights of an R peak and a T peak are reversed in the ECG waveform shown in FIG. 6B. In this case, an instruction to move an upper ECG electrode A (the upper node) in a left direction of a user by half a knuckle or one knuckle may be issued. A specific length (cm) may also be provided. When totally different ECG waveforms are obtained as shown in FIGS. 7A and 7B, an instruction to move both of two ECG electrodes in a lower direction by two knuckles may be issued.

Meanwhile, when it is determined that the judgment indicators values are not similar to the corresponding user-specific reference values as a result of the first similarity determination, an artificial intelligence learning model, which determines similarity by determining whether all the plurality of judgment indicators extracted in real time are present within a similarity range set through pre-learning, may be used. In other words, the similarity determiner 230 may further include an artificial intelligence model which determines, when it is determined that the judgment indicators values are not similar to the corresponding user-specific reference values as a result of the first similarity determination, similarity by determining whether all the plurality of judgment indicators extracted in real time are present within the similarity range set through pre-learning.

For reference, an area marked with dots in the ECG waveform shown in FIG. 8 indicates a similarity range which is set by learning a plurality of judgment indicators extracted from ECG data collected in the user-specific reference value setting mode. Also, the ECG waveform of a solid line exemplifies a normal ECG waveform which is within the similarity range and has a similarity of 95% or more, and the ECG waveform of a broken line exemplifies an abnormal ECG waveform which has a similarity of less than 95%.

When a similarity determination is made in the above-described manner, the electrode attachment position guide 240 informs the user of the attachment positions of the ECG electrodes according to the similarity determination result of each judgment indicator value (operation S70).

The electrode attachment position guide 240 may inform of the attachment positions of the ECG electrodes by displaying a body image, on which the attachment positions of the ECG electrodes are marked, on the information terminal display 440 of the user or may inform of the attachment positions of the ECG electrodes by a voice through the voice output part 450 of the user information terminal.

As described above, the system 200 for informing of the attachment positions of ECG electrodes according to the exemplary embodiment of the present invention informs of normal attachment positions when the attachment positions of ECG electrodes, which are attached to a user's body by a healthcare worker, are changed by the user. Accordingly, the user can be guided to obtain an ECG waveform at accurate positions.

In the above exemplary embodiment, an operation of informing of the attachment positions of ECG electrodes has been described. However, without any modification, the system 200 for informing of the attachment positions of ECG electrodes according to the exemplary embodiment of the present invention may store a plurality of judgment indicators extracted by the judgment indicator extractor 210 or ECG data transmitted from the wearable patch-type ECG measurement device 100 and then transmit the plurality of judgment indicators or the ECG data to the ECG analysis device 300 (operation S80).

In this case, the present invention only stores and transmits ECG data obtained at positions where ECG electrodes are initially attached by a healthcare worker. Consequently, it is possible to solve problems which may be caused by transmitting inaccurate ECG data, for example, misdiagnosis, overload of transmission data, and running efficiency degradation of a memory for storing and managing ECG data.

Although the present invention has been described above with specific content, such as specific elements, limited embodiments, and drawings, this is only provided to aid in overall understanding of the present invention. The present invention is not limited to the embodiments, and those of ordinary skill in the art can make various modifications and alterations therefrom. Therefore, the spirit of the present invention should not be limited to the described embodiments, and the following claims and all modifications and alterations equivalent to the claims fall within the scope of the present invention.

The invention claimed is:

1. A system for informing of attachment positions of electrocardiogram (ECG) electrodes, the system comprising:
   a judgment indicator extractor configured to extract a plurality of judgment indicator values from ECG data obtained through ECG electrodes;
   a reference value setter configured to, in a user-specific reference value setting mode, collect the judgment indicator values for a plurality of pieces of ECG data extracted by the judgment indicator extractor and set user-specific reference values for each judgment indicator;
   a similarity determiner configured to, in an ECG measurement mode, determine similarity by comparing a plurality of judgment indicator values extracted by the judgment indicator extractor with the user-specific reference values; and
   an electrode attachment position guide configured to inform a user of attachment positions of the ECG electrodes according to a similarity determination result of each of the judgment indicator values.

2. The system according to claim 1, wherein the reference value setter sets an average of each type of judgment indicator values as the user-specific reference value when an average variance of each type of judgment indicator values collected in the user-specific reference value setting mode is a reference value or less.

3. The system according to claim 1, wherein the reference value setter enters the user-specific reference value setting mode which is activated according to a user command and activates the ECG measurement mode after setting of the user-specific reference values is completed.

4. The system according to claim 1, wherein the similarity determiner, in the ECG measurement mode, determines first similarity by comparing the values of the judgment indicators having potential values among the plurality of extracted judgment indicator values with the corresponding user-specific reference values.

5. The system according to claim 4, wherein the similarity determiner includes an artificial intelligence model which determines, when it is determined that the judgment indicator values are not similar to the corresponding user-specific reference values as a first similarity determination result, similarity by determining whether all the plurality of extracted judgment indicators are present within a similarity range set through pre-learning in the ECG measurement mode.

6. The system according to claim 1, wherein the plurality of judgment indicator values include P peaks, R peaks, T peaks, RR intervals, QT intervals, QTc intervals, PR intervals, RT intervals, and QRS intervals of an ECG waveform.

7. The system according to claim 1, wherein the judgment indicator extractor, the reference value setter, the similarity determiner, and the electrode attachment position guide are a set of code data constituting an executable application program which is installed on an information terminal of an ECG measurement device user.

8. The system according to claim 1, wherein the electrode attachment position guide displays a body image, on which the attachment positions of the ECG electrodes are marked, on an information terminal display of an ECG measurement device user.

9. The system according to claim 1, wherein the electrode attachment position guide informs of moved attachment positions of the ECG electrodes by a voice through an information terminal of an ECG measurement device user.

10. A method of informing of attachment positions of electrocardiogram (ECG) electrodes which is executable on an information terminal of a user who uses a wearable patch-type ECG measurement device, the method comprising:

a first operation of extracting a plurality of judgment indicator values from each of a plurality of pieces of ECG data transmitted from the wearable patch-type ECG measurement device for a certain time;

a second operation of collecting the extracted judgment indicator values and setting a user-specific reference value for each judgment indicator;

a third operation of determining similarity by comparing a plurality of judgment indicator values, which are extracted from ECG data transmitted from the wearable patch-type ECG measurement device, with the user-specific reference values after the user-specific reference values are set; and a fourth operation of informing a user of attachment positions of ECG electrodes according to a similarity determination result of each of the judgment indicator values.

11. The method according to claim 10, wherein, when an average variance of each type of the collected judgment indicator values is a reference value or less, an average of each type of the judgment indicator values is set as the user-specific reference value.

12. The method according to claim 10, wherein the first and second operations are performed in a user-specific reference value setting mode which is activated according to a user command, and after the user-specific reference values are set, the third and fourth operations are repeatedly performed as an ECG measurement mode.

13. The method according to claim 10, wherein the third operation comprises:

determining first similarity by comparing the values of the judgment indicators having potential values among the plurality of judgment indicator values extracted from the ECG data transmitted from the wearable patch-type ECG measurement device with the corresponding user-specific reference values; and when it is determined that the judgment indicator values are not similar to the corresponding user-specific reference values, determining second similarity by determining whether all the plurality of judgment indicators are present within a similarity range set through pre-learning.

14. The method according to claim 10, wherein the plurality of judgment indicator values include P peaks, R peaks, T peaks, RR intervals, QT intervals, QTc intervals, PR intervals, RT intervals, and QRS intervals of an ECG waveform.

15. The method according to claim 10, wherein the fourth operation comprises displaying a body image, on which the attachment positions of the ECG electrodes are marked, on an information terminal display of the user.

16. The method according to claim 10, wherein the fourth operation comprises informing of moved attachment positions of the ECG electrodes by a voice through an information terminal of the user.

* * * * *